(12) United States Patent
Halbert et al.

(10) Patent No.: US 7,871,394 B2
(45) Date of Patent: Jan. 18, 2011

(54) SYSTEM AND METHOD FOR OPTIMIZING CONTROL OF PCA AND PCEA SYSTEM

(75) Inventors: Donald Halbert, San Diego, CA (US);
Robert D. Butterfield, Poway, CA (US);
Monte K. Fisher, Poway, CA (US);
Stephen Bollish, San Diego, CA (US)

(73) Assignee: CareFusion 303, Inc., San Diego, CA (US)

( * ) Notice: Subject to any disclaimer, the term of this patent is extended or adjusted under 35 U.S.C. 154(b) by 314 days.

(21) Appl. No.: 11/762,728

(22) Filed: Jun. 13, 2007

(65) Prior Publication Data

US 2007/0299389 A1    Dec. 27, 2007

Related U.S. Application Data

(60) Provisional application No. 60/813,429, filed on Jun. 13, 2006.

(51) Int. Cl.
*A61M 31/00* (2006.01)

(52) U.S. Cl. .............................. 604/67; 604/65; 604/66; 604/131; 604/151; 604/189; 604/500; 600/300; 600/522; 417/18; 705/2; 705/3; 705/4; 128/203.14

(58) Field of Classification Search ............. 604/65–67, 604/131, 151, 189, 500; 600/300, 522; 417/18; 128/303.13, 203.14; 714/745; 60/65–67, 60/131, 151, 189, 500
See application file for complete search history.

(56) References Cited

U.S. PATENT DOCUMENTS

| | | | |
|---|---|---|---|
| 4,459,582 A | | 7/1984 | Sheahan et al. |
| 4,710,163 A | * | 12/1987 | Butterfield ................... 604/65 |
| 4,743,228 A | * | 5/1988 | Butterfield ................... 604/505 |

(Continued)

FOREIGN PATENT DOCUMENTS

EP    1338295 A    8/2003

(Continued)

OTHER PUBLICATIONS

PCT International Search Report for International Application No. PCT/US2007/071151 mailed Nov. 23, 2007.

(Continued)

*Primary Examiner*—Nicholas D Lucchesi
*Assistant Examiner*—Scott Medway
(74) *Attorney, Agent, or Firm*—McDermott Will & Emery (57) ABSTRACT

In a patient controlled analgesia (PCA) system, physiological data is processed and alarms are provided by the controller of the physiological module sensing the data according to a first rule. The physiological data is also processed by a second, separate controller according to a second rule independent from the first controller. According to the second rule, the physiological data may be filtered, processed with physiological data and non-physiological data obtained from another source, such as a remote server, and the PCA delivery device controlled to prevent delivery of medication accordingly. The provided system of multiple processors and rules enables normal alarming by physiological sensor modules while the pausing or prevention of the PCA delivery is controlled by a separate controller. Through this means, not only are false pauses and alarms for PCA delivery reduced, but the normal alarms of the monitors are permitted to function normally.

24 Claims, 6 Drawing Sheets

U.S. PATENT DOCUMENTS

| | | | |
|---|---|---|---|
| 4,979,940 A * | 12/1990 | Bobo et al. | 604/503 |
| H001324 H * | 6/1994 | Dalke et al. | 604/65 |
| 5,343,868 A * | 9/1994 | Kurscheidt et al. | 600/486 |
| 5,348,008 A | 9/1994 | Bornn et al. | |
| 5,464,012 A * | 11/1995 | Falcone | 600/301 |
| 5,702,358 A * | 12/1997 | Witherspoon et al. | 604/6.1 |
| 5,733,259 A * | 3/1998 | Valcke et al. | 604/66 |
| 5,800,387 A | 9/1998 | Duffy et al. | |
| 5,957,885 A | 9/1999 | Bollish et al. | |
| 6,198,389 B1 | 3/2001 | Buccola | |
| 6,249,225 B1 | 6/2001 | Wang | |
| 6,379,312 B2 | 4/2002 | O'Toole | |
| 6,425,878 B1 * | 7/2002 | Shekalim | 604/65 |
| 6,572,545 B2 | 6/2003 | Knobbe et al. | |
| 6,579,231 B1 | 6/2003 | Phipps | |
| 6,689,091 B2 * | 2/2004 | Bui et al. | 604/67 |
| 6,780,322 B1 | 8/2004 | Bissler et al. | |
| 6,804,656 B1 * | 10/2004 | Rosenfeld et al. | 705/3 |
| 6,882,272 B2 | 4/2005 | Pfefferseder et al. | |
| 7,188,151 B2 * | 3/2007 | Kumar et al. | 709/217 |
| 7,220,240 B2 * | 5/2007 | Struys et al. | 604/65 |
| 7,462,786 B2 * | 12/2008 | O'Mahony et al. | 177/185 |
| 2001/0056358 A1 * | 12/2001 | Dulong et al. | 705/2 |
| 2002/0087113 A1 * | 7/2002 | Hartlaub | 604/65 |
| 2003/0106553 A1 | 6/2003 | Vanderveen | |
| 2003/0145854 A1 | 8/2003 | Hickle | |
| 2003/0214409 A1 | 11/2003 | Hickle | |
| 2004/0059234 A1 | 3/2004 | Martin et al. | |
| 2005/0126961 A1 | 6/2005 | Bissler et al. | |
| 2005/0171627 A1 | 8/2005 | Funk et al. | |
| 2005/0177096 A1 | 8/2005 | Bollish et al. | |

FOREIGN PATENT DOCUMENTS

| | | |
|---|---|---|
| WO | WO 2004/072828 A | 8/2004 |
| WO | WO 2005/056087 A | 6/2005 |

OTHER PUBLICATIONS

PCT International Preliminary Report on Patentability for International Application No. PCT/US2007/071151 dated Dec. 16, 2008.

* cited by examiner

SYSTEM AND METHOD FOR OPTIMIZING CONTROL OF PCA AND PCEA SYSTEM

BACKGROUND

The present invention relates generally to infusion systems and methods, and more particularly, to a system and a method for controlling the self-administration of analgesics to a patient while monitoring a physiological parameter of the patient.

Programmable infusion systems are commonly used in the medical field to deliver a wide range of drugs and fluids to patients in a variety of settings. For example, syringe pumps, large volume pumps (herein referred to as "LVP"), and flow controllers are used in hospitals, clinics, and other clinical settings to deliver medical fluids such as parenteral fluids, antibiotics, chemotherapy agents, anesthetics, analgesics, sedatives, or other drugs. Single or multichannel systems are available, and different systems have various levels of sophistication, including automatic drug calculators, drug libraries, and complex delivery protocols.

Still other types of drug delivery systems include a patient-controlled analgesia (herein "PCA") pump and a patient-controlled epidural analgesia (herein "PCEA") pump. With a PCA pump or PCEA pump, the patient controls the administration of the narcotic analgesics since the patient is usually in the best position to determine the need for pain control. PCA is commonly administered via a stand-alone infusion device dedicated solely for PCA use, such as a syringe pump having the required programming and patient request button or switch. Typically, the patient holds a button switch in his or her hand. The request button is wired or wirelessly connected to a PCA pump or separate controller that controls the PCA pump. When the patient presses the request button, the PCA pump or controller provides the patient with a programmed dose of analgesia or other medication. A PCA protocol program is contained in the PCA pump or separate controller and processes the patient request against various factors to determine if the analgesia requested by the patient should be administered.

Regardless of the type of pump system used, an undesirable side effect of the administration of drugs, particularly anesthetics, analgesics, or sedatives, can be central nervous system and respiratory depression. The ability to avoid overdosing such drugs is an important concern. While improvements have been developed in infusion systems where sophisticated automatic programming and calculation features have been designed to minimize medication programming errors, it is possible for patients to experience respiratory depression or other deleterious effects during the administration of narcotic analgesics or sedatives during in-patient or out-patient clinical procedures. Even in PCA applications, where overdoses are typically prevented by the patient falling asleep and therefore being unable to actuate a delivery button, there have been cases of respiratory and central nervous system depression associated with the administration of PCA. The causes include clinical errors in programming the PCA device, errors in mixing or labeling analgesics, device malfunction, and even overzealous relatives who administer extra doses of analgesics by pressing the dose request cord for the patient.

Because of the potential for respiratory or central nervous system depression due to narcotic analgesic overdose, narcotic antagonists such as naloxone (Narcan™) are widely available and commonly used in hospitals for reversal of respiratory and central nervous system depression. However, the effectiveness of such narcotic antagonists is highly dependent on prompt recognition and treatment of respiratory and central nervous system depression. Therefore, it would be desirable to monitor the actual physical condition of the patient to find respiratory or nervous system depression so that immediate remedial measures may be taken.

For the detection of potential respiratory depression associated with the administration of narcotic analgesics, sedatives, or anesthetics, a system that indicates a patient's respiratory status and cardiac status without the need to invasively measure or sample the patient's blood is particularly desirable and useful. Non-invasive end tidal carbon dioxide ("$EtCO_2$") and pulse oximetry ("$SpO_2$") monitoring are two technologies used to monitor physiological parameters of a patient. The $EtCO_2$ method monitors the concentration of exhaled and inhaled $CO_2$, respiration rate, and apnea (respiration rate of zero) while pulse oximetry monitors the oxygen saturation of a patient's blood and the patient's pulse rate. The combination of $EtCO_2$ concentration, respiratory rate, and apnea or the combination of the blood oxygen saturation and pulse rate can be important indicators of overall patient respiratory and cardiac status.

One common approach to non-invasive pulse oximetry uses a dual-wavelength sensor placed across a section of venous tissue such as a patient's digit to measure the percentage of hemoglobin oxygenated in the arterial blood, and thereby estimates the patient's oxygen saturation level. In addition, since the oxygenated hemoglobin at a specific tissue position is pulsatile in nature and synchronous with the overall circulatory system, the system indirectly measures the patient's pulse rate. Examples of similar pulse-oximetry sensors are disclosed in U.S. Pat. No. 5,437,275 to Amundsen et al. and U.S. Pat. No. 5,431,159 to Baker et al., incorporated herein by reference.

Another means of monitoring the respiratory status of a patient is by measuring and charting $EtCO_2$, a procedure known as capnography. In particular, current capnography devices utilize spectroscopy, for example infrared, mass, Raman, or photo-acoustic spectroscopy, to measure the concentration of $CO_2$ in air flowing through a non-invasive nose and/or mouthpiece fitted to the patient (for example, see U.S. Pat. No. 6,379,312 to O'Toole). Capnographic $EtCO_2$ waveforms and indices such as end tidal $CO_2$ concentration, or the concentration of $CO_2$ just prior to inhaling (also referred to as fractional concentration of carbon dioxide in inspired gas or "$FICO_2$") are currently used to monitor the status of patients in operating rooms and intensive care settings.

Patient care systems providing for central control of multiple pump modules, including PCA modules, are known in the medical field. Such a care system generally provides a controller which interfaces with a plurality of individual pumps to provide various control functions. An improved patient care system of this nature is disclosed in U.S. Pat. No. 5,713,856 to Eggers et al., incorporated herein by reference. The central management unit of the Eggers et al. system can, for example, obtain infusion parameters for a particular infusion module from the clinician and serve as an interface to establish the infusion rate and control the infusion by that infusion module accordingly. It can individually control the internal setup and programming of each functional module, and receive and display information from each functional module. The Eggers et al. patient care system also provides for the central control of various monitoring apparatus, such as pulse oximeters and carbon dioxide monitors.

In more advanced systems that have provided substantial benefit to the art, control over a PCA system is provided in conjunction with monitoring a patient's physiological parameter or parameters. In the case of U.S. Pat. No. 5,957,885 to Bollish, a pulse oximetry system is disclosed and in the case of U.S. Application Pub. No. 2003/0106553 to Vanderveen, a EtCO2 system is provided. Both of these systems have provided a substantial improvement in the art. Improvements to those and other systems have been provided by U.S. Application Pub. No. 2005/0177096 to Bollish, Brook, and Steinhauer, incorporated herein by reference. Improvements include providing a trend of respiration or pulse rate with the dosing of the analgesic superimposed so that a trend of the patient's physiological parameter and response can be seen clearly and rapidly. Additionally, improvements include expanding a drug library to specifically include various PCA dosing parameter limits.

Furthermore, the system in accordance with the above provides automatic inhibition of patient-requested medication (referred to hereafter as "pausing") of the PCA module in the event of respiratory depression. Without automatic PCA pausing, continued administration of the narcotic analgesics may aggravate respiratory depression until appropriate medical personnel arrive to intervene. The time it takes for medical personnel to recognize a problem and intervene will delay administration of narcotic antagonists and thereby potentially compromise their effectiveness.

Improvements to PCA systems in which patient physiological data is considered in real time permit further benefit from the PCA system. Patients can receive treatment while an automatic PCA shut-off or "pausing" feature lessens the risk of inadvertent respiratory depression. However, it has been noted that unwanted pausing of PCA infusions can occur due to false alarms. Under the programming of at least one system, a PCA system that has been automatically paused cannot be restarted without manual reset of the system by a clinician. During this "paused" period, the patient is unable to receive analgesia or other treatment desired.

False alarms are typically caused by transient, short term physiological and electrical artifacts in monitored data. False alarms are undesirable because they result in the PCA system pausing inappropriately depriving the patient of needed pain medication. They also place additional burden on caregivers to investigate the event and re-activate the system.

Hence, those skilled in the art have recognized a need for an improved patient care system and method that can monitor the physical condition of a patient and can control the infusion of PCA or PCEA to the patient based on the analysis. Further, those skilled in the art have recognized a need for an improved patient care system and method that can not only automatically pause a PCA or PCEA system, but also lessen the risk of false pausing episodes. The present invention fulfills these needs and others.

SUMMARY OF INVENTION

The invention is directed to the reduction or elimination of false monitoring alarms regardless of whether they affect any PAUSE function, and to the reduction or elimination of false PAUSE activation. In a more detailed aspect, the invention is directed to a system and method to minimize false monitoring alarms and pausing of PCA infusions due to transient, short term physiological and electrical artifacts occurring in physiological monitoring data. It further provides methods for the optimal automation of patient controlled infusion pumps through use of patient monitoring data and pharmacokinetic modeling of the patient's drug disposition.

In accordance with aspects of the invention, there is provided a system for optimizing control over PCA and PCEA devices configured to deliver medication, comprising a medication delivery request device with which a request signal for delivery of the medication is provided, a physiological device configured to provide a physiological signal representative of physiological data, a first controller that receives the physiological signal, processes the physiological signal and provides a first monitoring alarm signal according to a first, a first alarm device that communicates the first alarm signal, and a second controller, separate from the first controller, that receives the request signal, receives the physiological signal, processes the request signal and the physiological signal and controls the operation of the PCA device according to the processing to deliver medication in accordance with a second rule, wherein the second rule is different from the first rule. In a further aspect, the second controller controls the PCA device according to the processing to a non-delivery mode in which the PCA device does not deliver medication. In yet another aspect, the system comprises a second alarm device that communicates a second alarm in response to a second alarm signal, wherein the second controller provides the second alarm signal according to the processing under the second rule.

In accordance with more detailed aspects, the physiological data device comprises a physiological monitor that measures a physiological parameter and provides the physiological signal representative of the measured parameter. The system further comprises a physiological parameter data base of previously-determined patient-specific data related to a physiological parameters, wherein the data base provides a data signal representative of data related to a previously-determined patient-specific physiological parameter, the second controller receives the request signal, receives the physiological signal, receives the data signal, and processes the request signal, the physiological signal, and the data signal, and controls the operation of the PCA device in response to the processing to deliver medication in accordance with the second rule.

In yet a further detailed aspect, the system further comprises an input device with which to modify the second rule. In one case a remote server is connected with the second controller, wherein the second controller receives a modification to the second rule from the server and processes in accordance with the modified second rule. The second controller receives further patient-specific data from the server and processes the patient-specific data, the request signal, the physiological signal, and controls the operation of the PCA device in accordance with the processing to deliver medication in accordance with the modified second rule. The second controller controls the PCA device according to the processing to a paused mode in which patient originated dose requests are inhibited or in which both patient originated dose requests and clinician ordered doses (bolus or basal) are inhibited.

In other aspects, the second controller filters the physiological signal according to one or more of an moving average filter, a rate of change filter and cumulative average, an impulse response filter, a statistical filter, and an adaptive filter. Processing based on the patient's drug disposition predicted by pharmacokinetic state may also be performed. In one case, a parameter of a filter is adapted in accordance with historical data related to a physiological parameter and in another, a parameter of a filter is adapted in accordance with concomitant data related to medication infusion.

In accordance with a method, there is provided a method for optimizing control over a PCA device configured to deliver medication, comprising receiving a medication request signal for delivery of the medication, receiving a physiological signal representative of physiological data, processing the physiological signal with a first controller and providing a first alarm signal according to a first rule, communicating the first alarm signal, and processing the request signal and the physiological signal with a second controller separately from the first controller and controlling the operation of the PCA device according to the processing to deliver medication in accordance with a second rule, wherein the second rule is different from the first rule.

In accordance with more detailed method aspects, the step of controlling the operation of the PCA device comprises controlling the PCA device according to the processing to an inhibitory or paused mode in which the PCA device does not deliver medication on demand of the patient or does not deliver clinician programmed doses. In another aspect, the method further comprises providing a second alarm signal according to the processing under the second rule. Further, the step of receiving a physiological signal representative of physiological data comprises measuring a physiological parameter and providing a physiological signal representative of the measured parameter. In another aspect, the method for optimizing control further comprises receiving a physiological data signal by the second controller representative of physiological data from a physiological parameter data base of previously-determined patient-specific data related to a physiological parameter and processing the data signal, the request signal, the physiological signal by the second controller, and controlling the operation of the PCA device in response to the processing in accordance with the second rule.

In yet further aspects, the method comprises modifying the second rule by use of an input device connected with the second controller. The step of modifying the second rule comprises modifying the second rule by a remote server and processing by the second controller comprises processing in accordance with the modified second rule. The method further comprises receiving further patient-specific data from the second server and processing the patient-specific data, the request signal, the physiological signal by the second controller and controlling the operation of the PCA device in accordance with the processing to deliver medication in accordance with the modified second rule.

These and other features and advantages of the present invention will become apparent from the following detailed description of the preferred embodiments which, taken in conjunction with the accompanying drawings, illustrate by way of example the principles of the invention.

DETAILED DESCRIPTION OF PREFERRED EMBODIMENTS

Figure 1:
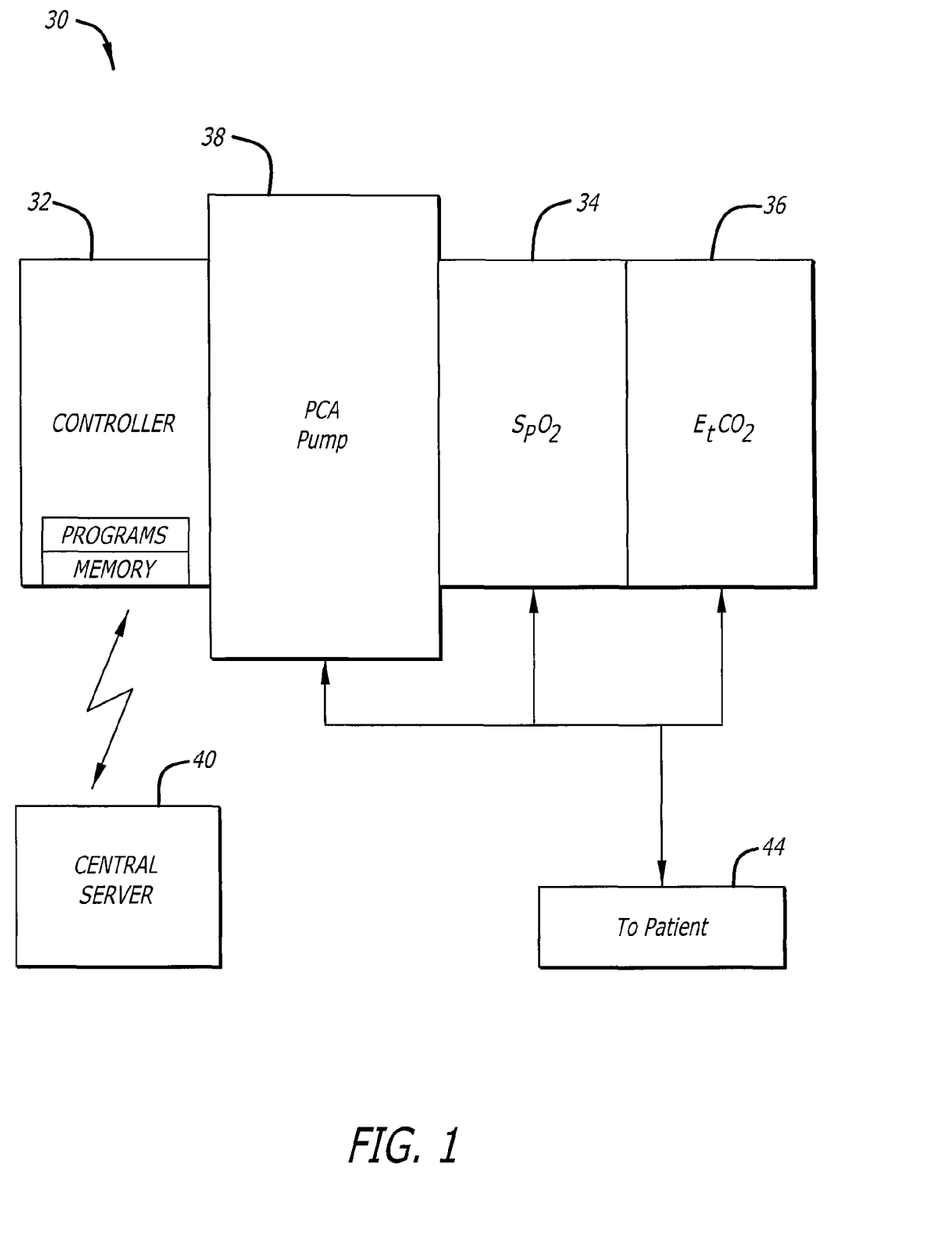
FIG. 1 is a block diagram view of an embodiment of a patient care system according to aspects of the present invention showing a pump module labeled as "PCA", an EtCO2 monitoring module, an SpO2 monitoring module, and a programmable control unit ("controller") interconnecting the pump module, the SpO2 monitoring module, and the EtCO2 monitoring module, and an optional central server that may be located elsewhere communicating by wire or wirelessly with the controller.

Referring now in more detail to the drawings for purposes of illustration, wherein like reference numerals designate corresponding or like elements among the several views, there is generally shown in FIG. 1 an embodiment of a modular drug infusion and monitoring system 30 comprising a program module 32, one or more patient monitoring devices (such as an SpO2 module 34 and an EtCO2 module 36 as shown), and a patient-controlled analgesia ("PCA") pump 38 that may take the form of a syringe driver device for infusing the contents of a syringe into a patient as requested by the patient with a hand-held button for example, under the control of the program module 32 or an optional central server 40, shown as being connected to the program module 32 wirelessly. When operational, the SpO2, EtCO2, and PCA pump are connected to a patient 44.

Figure 2:
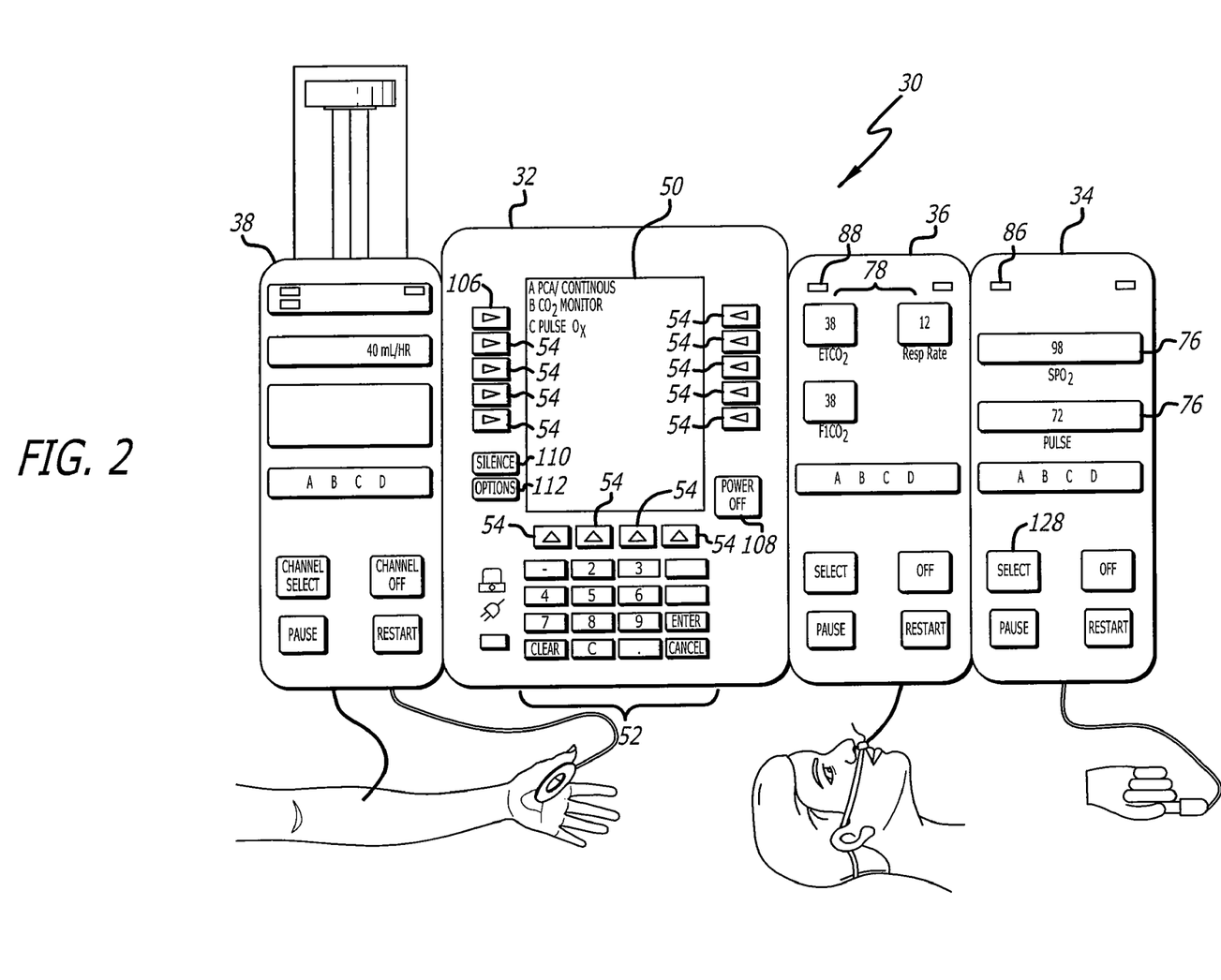
FIG. 2 is an elevation diagram showing the use of a controller in operational connection with a PCA pump, an EtCO2 monitoring module, an SpO2 monitoring module, a central server similarly to FIG. 1, and showing actual patient interaction with the system.

The program module 32 includes memory and programs and, as an embodiment, may be described in terms of the advanced interface unit (100) found in U.S. Pat. No. 5,713,856 to Eggers incorporated herein by reference. The program module generally performs four functions in the patient care system 30. It provides a physical attachment of the system 30 to structures such as IV poles and bed rails. It provides power to the system 30. It provides an interface between the system 30 and external devices, and, except for certain specific information, it provides a majority of the user interface with the system 30. Referring now to FIG. 2, the program module 32 contains an information display 50, which may be any type of display such as a liquid crystal display. The display may be used during setup and operating procedures to facilitate data entry and editing. The display may also be used to display various operating parameters such as volume to be infused (VTBI) for individual infusion pump functional modules 38 and the current time of day, as well as other prompts, advisories, and alarm conditions. The program module 32 contains a plurality of hardkeys 52 and softkeys 54 for entering data and commands. The numerical hardkeys are used for entering numerical data, while the remainder of the hardkeys, as well as the softkeys, are used for entering operational commands.

Figure 3:
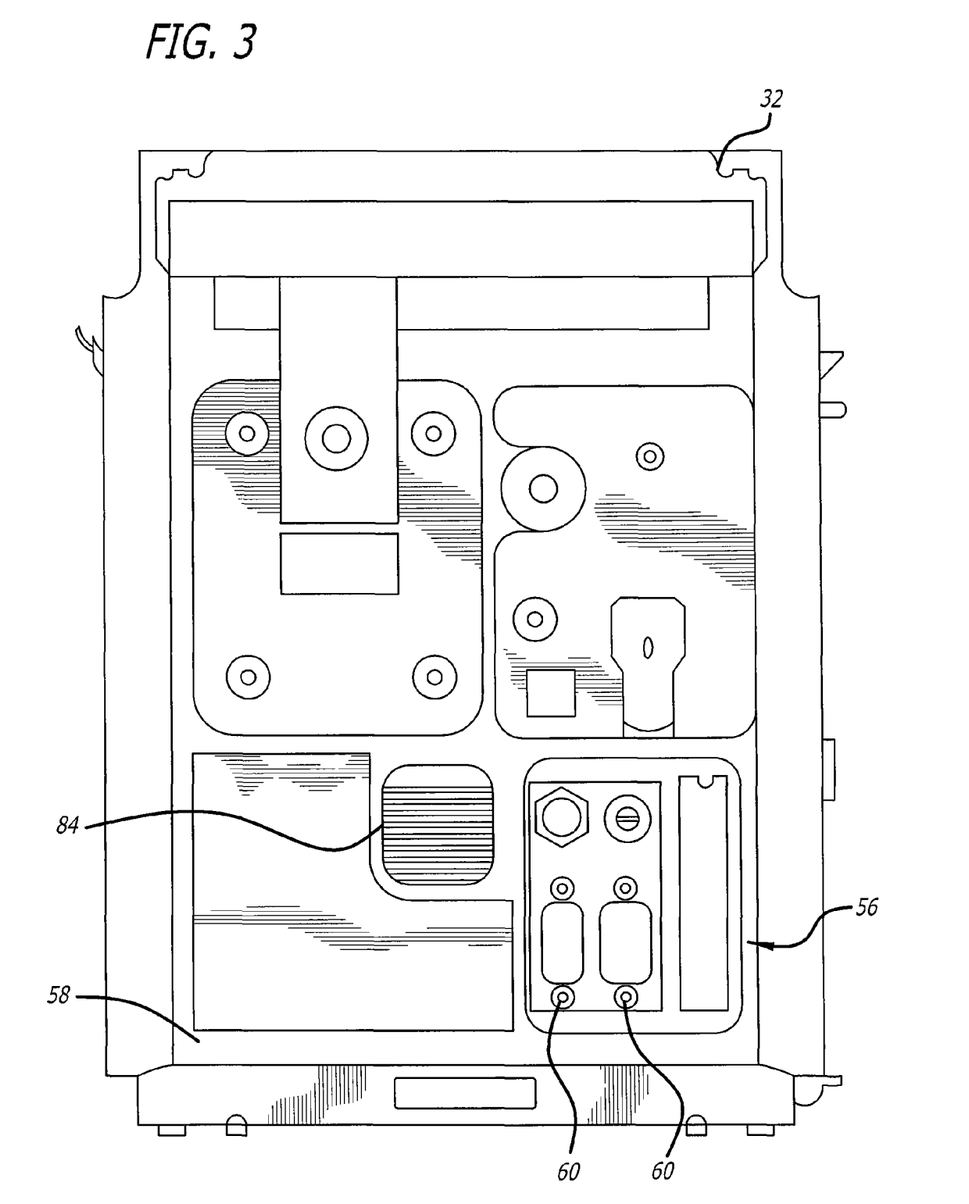
FIG. 3 is an elevation diagram of the back panel of the controller of FIG. 2 showing various data communication ports and other devices.

Referring also to FIG. 3, the program module 32 preferably also contains at least one external communication interface 56 is located at the rear panel 58 of the controller. The communication interface is preferably includes an industry standard personal computer memory card international association (PCMCIA) slot for receiving PCMCIA cards, although one skilled in the art could select from a variety of commercially available communication means. Alternatively, it may be built into the housing of the controller and communicate wirelessly. Also located at the rear of the controller is at least one interface port 60. Interface ports are preferably industry standard RS-232 or USB ports, although one skilled in the art could select from a variety of commercially available communication means. It is to be understood that although a preferred embodiment of the invention is described as containing an interface 56 and at least one port 60, any number or combination of communication interfaces and ports could be included in the controller. A wireless interface may also be used.

The interface 56 and the ports 60 illustratively may be used to download drug libraries, drug delivery profiles, and other system configuration values, or may be used to upload event history data from the program module 32. The interface and the ports may also act as an interface to patient monitoring networks and nurse call systems or as an interface to external equipment such as barcode readers to provide a means of inputting drug and/or patient information from medication or patient records. Performing these functions with the interface and the ports will advantageously provide greater functionality and adaptability, cost savings, and a reduction in input errors. The interface and the ports may also be supplemented with a Patient Controlled Analgesia (PCA) port (not shown in FIG. 3) although it may take the form of an RS-232, USB, wireless, or other connection. The PCA port would provide a connection to a remote hand-held "dose request" button which can be used by a patient to request a medication dose during PCA applications. Alternatively, the PCA port may be located in a functional module 38 as shown in FIG. 2 where it is part of the syringe pump designed for PCA operation.

The interface 56 or a port or ports 60 can also be used to download complex drug delivery profiles, or infusion protocols such as PCA or PCEA protocols, to the patient care system 30. Various drug delivery profiles are known within the medical field. As is the case in the downloading of drug libraries, complex drug delivery profiles can be created and then stored on PCMCIA memory cards. A PCMCIA interface can then be used to download the drug delivery profiles to the system, where they can then be stored in permanent or semi-permanent memory within the program module 32.

Figure 4:
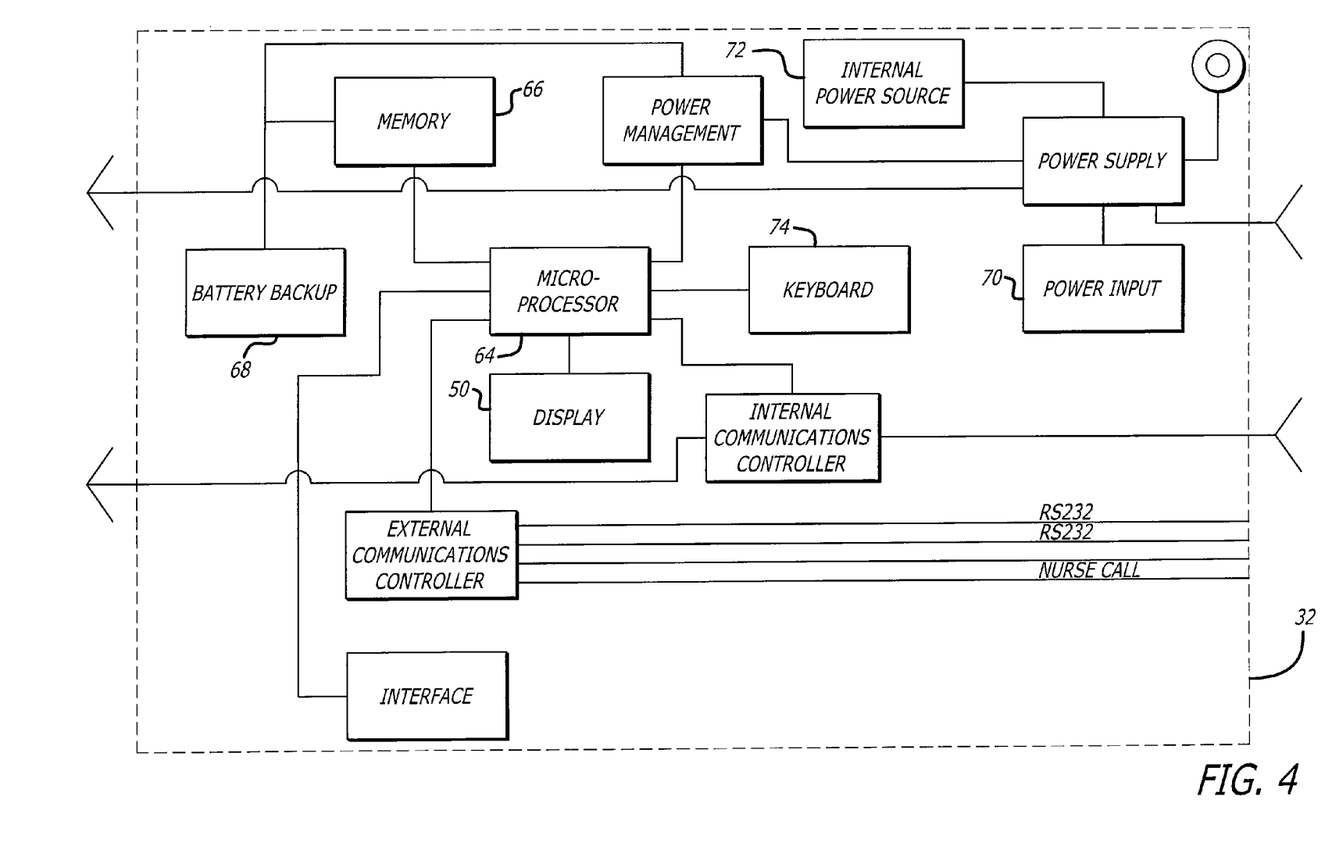
FIG. 4 is a block circuit diagram of the controller of FIG. 2 showing internal functions of the controller.

Referring now to FIG. 4, a microprocessor 64 and a memory 66 of the program module 32 receive and process data and commands from the user, as well as communicate with and control functional modules and other devices external to the system. It is to be understood that that memory of FIG. 4, as well as other memories in the patient care system 30, may be any type of memory or any combination of memories that can be erased and reprogrammed without having to physically remove the memory from the system. Examples of such memories include, but are not limited to, battery-backed random access memory (RAM) and "flash" electronically erasable programmable read only memory (FLASH EEPROM). Certain memory may also be read-only memory (ROM) as necessary. A battery backup 68 provides power to the memory to maintain the information stored in the memory in the event of loss of power from both the power input 70 and the internal power source 72. The controller also contains a keyboard 74 (comprising hardkeys 52 and softkeys 54) and a display 50 as discussed in conjunction with FIG. 2.

It is to be further understood that the functional modules, such as the SpO2 module 34 and the EtCO2 module 36 shown in FIGS. 1 and 2, in this embodiment also have processors and memory. Identification information must always be stored in the memory of each functional module. The identification information includes a means for uniquely identifying each functional module, preferably a serial number, so that, for example, the event history of each functional module can be followed and uploaded. The identification information also includes a means for identifying to the program module 32 the function of the functional module, such as a code to indicate that the functional module is, for example, a PCA pump. This information allows a program module 32 storing a plurality of software domains to know which domain to access for the selected functional module. Thus, the identification information stored in each functional module not only uniquely identifies the functional module to an attached interface module, but identifies the functions of the functional module as well. This identification information, as well as the software domain corresponding to a type of functional module comprises information specific to each functional module.

Functional modules, especially when they are physiological monitors, may contain their own internal programs in their own memory. For example, certain SpO2 and EtCO2 monitors are distributed by manufacturers in the form of a sensor with an accompanying "board" sold as a set. The accompanying board includes a processor, memory, and programming for processing the associated sensor's data. The board is typically located in the functional monitor module 34 and 36 for example and is capable of providing data for a display and for alarms. Examples of such displays are shown in FIG. 2 where both functional modules 34 and 36 display data 76 and 78 respectively associated with their particular sensors. Such sensor/board sets include their own sets of rules for processing data produced by their respective sensors including rules concerning when to provide alarms. However, they may not provide specific processing for pausing a PCA module based on the sensor's data. In the past, alarms provided by the sensor/board set may have been used to pause a PCA pump. Such pausing based on the internal processor, programming, and rules of the sensor and board set for providing alarms have resulted in false alarms and unnecessary pausing, as discussed in the Background section of this document.

In an effort to reduce the number of unnecessary pauses of a PCA pump due to false alarms, a system and method have been provided in accordance with the present invention that specifically process sensor data to determine if pausing a PCA or PCEA pump is needed. Turning now to the embodiment shown in FIG. 5, a controller 80 is shown such as that shown in FIGS. 1 and 4 that includes internal memory (not shown) and a processor (not shown) configured to store and execute a PCA Control Protocol program 82 with its own independent and distinct rules, apart from those contained in monitoring modules 34 and 36 that may provide alarms. The PCA Control Protocol 82 accepts data input from one or more selectable patient monitoring modules such as the SpO2 module 34. Based on such data input from selected patient monitoring modules, the PCA Control Protocol may alter the PCA infusion by pausing, alarming, or resuming. A further ability of the PCA Control Protocol 82 is titration of infusions including bolus amount, basil rate and refractory period. Additionally, titration by the PCA Control Protocol may also be based on pharmacokinetic ("PK") model estimates of serum, muscle, fat, effect-site concentrations, or similar body compartments. Titration may further be based on response(s) of patient vital signs to drug infusion (including bolus and basil levels).

Premonitory drug library warnings (directed to the caregiver) from the PCA Control Protocol 82 are derived from analysis of the patient's response to drug infusion. Such warnings may be caused by a patient response that is outside a stored limit or a stored acceptable range where such range forms a part of a drug library to which the program module 32 has access. Such drug libraries may be stored in the program module 32, or in a monitoring module or modules 34 or 36, or in the central or remote server 40 (FIG. 1), or elsewhere. They may be located in a handheld unit of a clinician. For a more detailed description of drug libraries and their use, refer to U.S. Pat. No. 5,681,285 to Ford, incorporated herein by reference.

Further, the PCA Control Protocol 82 may provide audible and visual feedback to the patient and clinicians. Visual feedback may be provided through the displays 50, 76, 78 on the program module 32 and the monitoring modules 34 and 36 as shown in FIG. 2. Audible feedback may be provided by a speaker 84 such as that shown in the rear panel diagram, FIG. 3, for the program module 32. Such feedback may include warnings of impending adverse conditions such as respiratory depression and may inform those in the vicinity regarding availability of a patient-controlled dose. That is, one or more displays, such as 50 on the program module 32, may state in text or graphically that a PCA dose is available. Audibly pleasing tones or speech may also be provided by the controller or other unit to indicate to the patient that a PCA dose is available to be requested by the patient.

Figure 5:
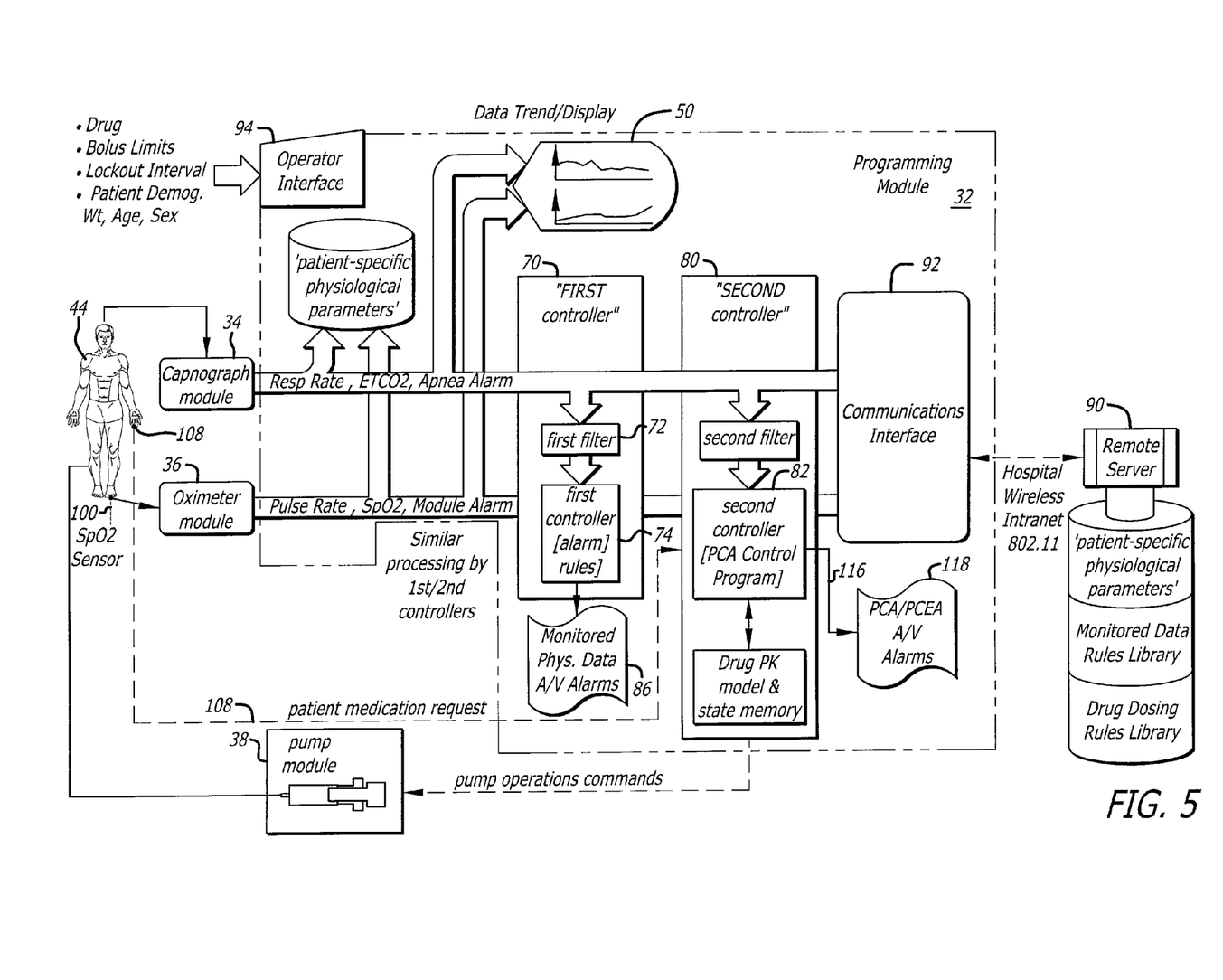
FIG. 5 is a block diagram in accordance with aspects of the present invention showing physiological monitors connected with a first controller and a second controller, and the program module control over a PCA pump and displays, as well as connection to a remote server either by wired means or wirelessly.

In accordance with an aspect of the invention, and referring briefly to FIG. 2 as well as FIG. 5, individual patient monitoring modules 34 and 36 may be configured to alarm distinctly and apart from the PCA Control Protocol alarming configuration. Such alarms may take the form of lights 86 and 88 on the front panels of the monitoring modules 34 and 36 and may be audible as well. The alarms may also be transmitted to the remote server 90 directly and independently by the monitoring modules or through the controller 80 through a wired or wireless connection with the server. Additionally, the PCA Control Protocol 82 may retrieve and consider data obtainable from the remote server 90 such as patient lab data and pre-existing conditions of the patient, such as chronic obstructive pulmonary disease ("COPD"). For example, the PCA control protocol 82 may be initially set to relatively low PCA pause limit levels when the server provides data indicating that the patient has COPD. The clinician may then alter the PCA pause limits and rules of the PCA control protocol through an input device such as a PDA or keyboard or other data communication device if desired based on actual observations of patient condition and reactions to PCA. Further, the PCA Control Protocol's initial rules and/or configuration may be altered or optimized by the central server 90 based on additional information the central server possesses concerning the patient or rules or other.

As mentioned briefly above, data input, rule changes, or limit changes may be directly entered into the PCA Control Protocol through a data input device (operator interface) 94. For example, the current PCA pause limits have been initially set by the clinician or server 90 to a relatively low level when the clinician enters a high standardized pain score for the patient. Subsequent examination of the patient and his or her reactions to PCA activities may prompt the physician to change the pause limits.

Referring further to FIG. 5, the SpO2 sensor 100 communicates its output to the SpO2 module 34 for processing. The SpO2 module in turn communicates sensor data to the controller 80. In one embodiment, the SpO2 module will communicate an alarm, in this case wirelessly, to the server 90. The alarm of the SpO2 module may also be communicated to the server through the controller and its own wireless connection 92 to the server. Also in the event of an alarm provided by the SpO2 module, an alarm displays 86 (FIG. 2). Furthermore, raw SpO2 data 102 may be communicated from the SpO2 module to a main data display, such as the display 50 in the controller of FIG. 2. Alarms generated by the SpO2 module 34 are generated as a result of data processing according to a first set of rules located in the sensor 100 and/or the SpO2 module 34. A first processor 70 uses a first filter 72 for processing data, along with alarm rules 74, from which audio/visual alarms are provided 86.

Data from the SpO2 module is communicated to the controller 80 for processing according to a second set of rules forming part of the PCA protocol 82. The second set of rules may be a basic set programmed into the memory of the controller and may be changed by clinician input 94, or by server 90 input, or by other means. The data represents a physiological condition of the patient and is processed by the controller. After processing, the data 103 is made available to the display 50. As shown in FIG. 5, a display switch 104 is provided that permits a clinician to select for display data from the SpO2 module or data processed by the controller.

Figure 6:
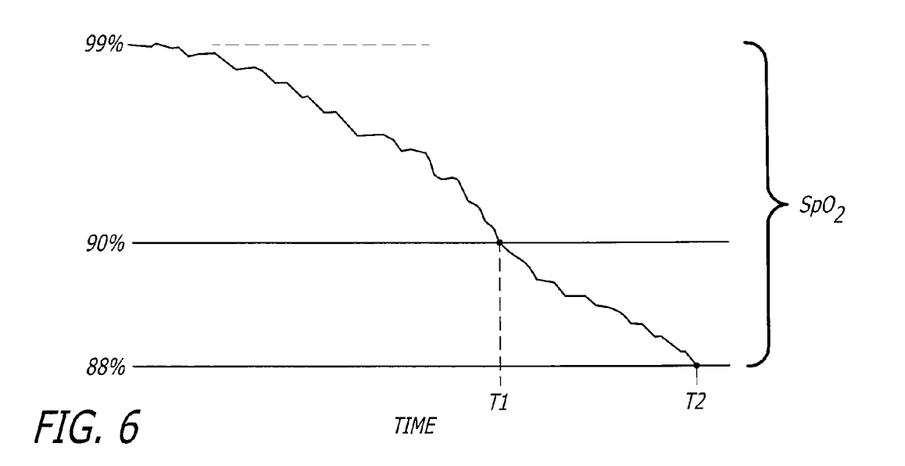
FIG. 6 is an SpO2 waveform showing significant points over time that may be used to trigger alarms or to pause a PCA pump.

The data processed by the controller 80 is also subjected to certain logic that may be internal to the controller or located elsewhere, such as in a PCA pump 38 for example. As an example, a first logic is enabled, i.e., a signal is provided from it 80 to the PCA pump 38 to provide a dose of medication to the patient, when the patient dose request button 108 is activated and when the patient data 103 as processed by the controller is at a certain level. Referring now additionally to FIG. 6, a graph of a patient's SpO2 level is presented according to time. At time T1, the patient's SpO2 level has fallen from 99% to 90%. According to a rule of the controller 90, such a decrease to 90% may be the threshold at which a patient's PCA is paused. Such a level is indicated on FIG. 5 by the signal line labeled T1. Therefore when T1 is reached, even if processed data 103 is provided by the controller 80, the PCA pump 38 will be "paused."

The same approach is performed for alarms based on the data as processed by the second set of rules contained in the controller 80. Referring again to FIG. 6, the patient's SpO2 level is shown as falling to 88% at T2. At this level, the rules in the controller may require an alarm, in addition to the already engaged pause of the PCA device 38. Logic will then trigger an alarm output 116 that is processed by the controller prior to its presentation visually 118 and/or audibly (not shown) on an alarm display. Such a display may be presented by the display 50 of the program module 32 in FIGS. 2 and 5 as an example, in text form, graphic form, and/or with blinking lights. The controller 80 may also conduct the alarm signal to the server 90.

The above alarm/pausing protocol is a simplistic example that depended on only the input of SpO2. It should be understood that the data from the SpO2 module as well as from other modules and other sources of non-real time physiological data, such as allergies from the server 90, may actually be processed by the controller as well. For example, the PCA controller Protocol may filter patient data input from the monitoring modules 34 and 36 to the PCA Control Protocol in the following manner:

a) a finite impulse response averaging filter (e.g. one-minute to two-minute moving average or 'boxcar' filter);

b) a filter based on the rate of change (derivative) and cumulative average (integral) of the data as well as its present value;

c) a general FIR (finite impulse response) or IIR (infinite impulse response) digital filter;

d) a statistical filter such as a "median" filter; or e) an adaptive filter such as a Kalman type.

In one embodiment, the above classes of filters may have their parameters adapted in accordance with historical and concomitant data sources besides the vital sign data, such as:

a) an adaptive filter employing the frequency and duration of prior alarm events;

b) an adaptive filter employing the total amount of drug infused; or c) an adaptive filter employing estimates of plasma and/or effect site concentrations (Cp, Ce) of the analgesic medication, such estimates made through use of appropriate pharmacokinetic ("PK") models, the PK effect site estimates being employed to modify the characteristics (poles and zero's) of the filter.

One example of such an adaptive filter is a boxcar filter whose window length is a function of the effect site concentration (Ce) of the drug relative to a normal therapeutic level. This would make the filter more sensitive when the patient's effect site level rises above the normal therapeutic level. For example, when a patient's effect site level is above the normal therapeutic level, the window length or averaging period of the boxcar filter is reduced.

The above filtering may be according to the rules in the controller; however, those rules and the filtering performed as a result can be selected, configured, or supplied by the central server 90 based on information and logic contained on the central server or to which it has access. In another embodiment, a central server could be used to control the PCA Control Protocol logic.

Figure 7:
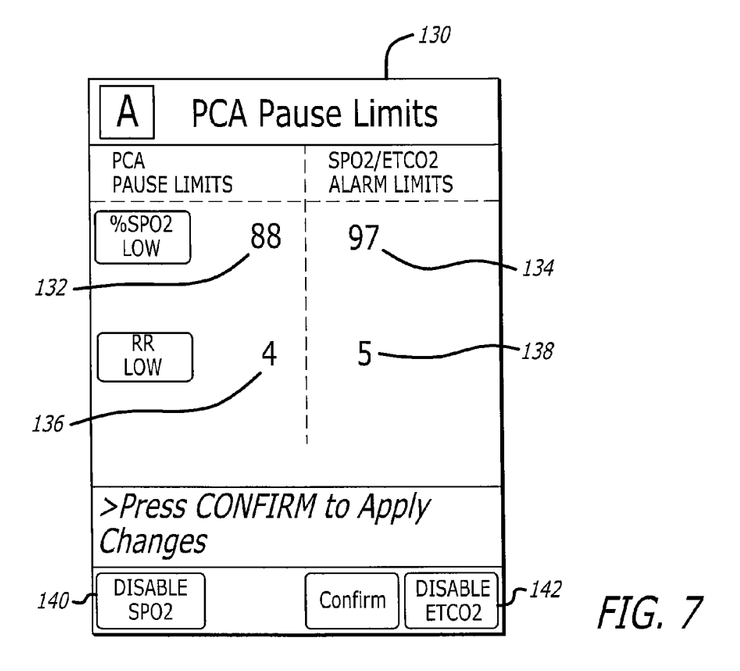
FIG. 7 is an enlarged display of a control screen that may be presented on the controller of FIG. 1 showing "PCA PAUSE LIMITS" along with "SpO2/EtCO2 ALARM LIMITS" with the display permitting control over the limits.

Referring to FIG. 7, the display 50 of the controller of FIG. 2 is shown. The PCA Control Protocol also provides "PCA PAUSE LIMITS" for the SpO2 and EtCO2 monitoring modules 34 and 36 that are independent of the SpO2 and EtCO2 monitoring modules' own alarm limits. The display screen of FIG. 7 shows a display screen 130 with four limits. A pair of limits for the SpO2 monitoring module 34 includes a PCA PAUSE LIMIT 132 of "88," which is provided by the PCA Control Protocol, and an SpO2 ALARM LIMIT 134 of "97." Accordingly, an alarm signal will be generated by the PCA Control Protocol 82 (FIG. 5) when the patient's SpO2 level reaches or falls below "97," and another alarm signal will be generated by the PCA Control Protocol and drug delivery by the PCA infusion pump 38 (FIG. 2) will pause when the percent SpO2 level reaches or falls below "88." The alarm signal occurring at the limit of 97 may be inaudible to or otherwise unnoticeable by the patient and may be transmitted to a nurse station or other remote location to alert a clinician and so as not to disturb the patient. Alternatively, the alarm signal occurring at the limit of "97" may be audible or visible to the patient so as to provide an early warning that drug infusion may soon be paused, or to wake up the patient.

FIG. 7 also shows a pair of limits for the EtCO2 monitoring module 36 that includes a PCA PAUSE LIMIT 136 of "4," which is provided by the PCA Control Protocol, and an EtCO2 ALARM LIMIT 138 of "5." Accordingly, an alarm will sound when the patient's respiration rate ("RR") reaches or falls below "5" and drug delivery by the PCA infusion pump will pause when the respiration rate reaches or falls below "4." As with the SpO2 limits, the alarm signal occurring at the limit of "5" may be inaudible to or otherwise unnoticeable by the patient and may be transmitted to a nurses station or other remote location to alert a clinician and so as not to disturb the patient. Alternatively, the alarm signal occurring at the limit of "5" may be audible or visible to the patient so as to provide an early warning that drug infusion may soon be paused or to wake up the patient.

The display screen 130 of FIG. 7 may also be used by a clinician to remove either one or both of the SpO2 and EtCO2 monitoring modules 34, 36 from the PCA Control Protocol. Removal of the SpO2 and EtCO2 modules occurs independently of the monitoring modules being active in the system. When a monitoring module is removed, such as by pressing the "Disable" key on the display 130, but is active, the alarm signal associated with PCA Pause Limit is disabled for producing a noticeable alert or alarm event while the monitoring module remains powered and continues to take measurements.

Referring again to the keys of FIG. 7, an oximetry soft key labeled DISABLE SpO2 140 that can be actuated by a clinician to conveniently disable the alarm signal associated with PCA Pause Limit for the SpO2 monitoring module 34 so that no alarm event occurs even if the sensed percent SpO2 level appears to reach or fall below "88," such as when the sensor connected to the patient is temporarily disconnected to allow the patient to leave the bed momentarily. When the oximetry soft key 140 is actuated, it is labeled ENABLE SpO2. The clinician may actuate the oximetry soft key 140 again to enable the alarm limit associated with PCA Pause Limit for the SpO2 monitoring module 34. In this way, the SpO2 monitoring module 34 need not be turned off when the patient leaves and turned on again and reset when the patient returns.

A capnography control device or capnography soft key labeled DISABLE EtCO2 142 can be actuated by a clinician to conveniently disable the alarm signal associated with the PCA Pause Limit for the EtCO2 monitoring module 36 so that no alarm event occurs even if the sensed respiration rate appears to reach or fall below "4," such as when the connection to the patient is temporarily removed to allow a patient to eat a meal. When the capnography soft key 142 is actuated, it is labeled ENABLE EtCO2. The clinician may actuate the capnography soft key 142 again to enable the alarm limit associated with PCA Pause Limit for the EtCO2 monitoring module 34. In this way, the EtCO2 monitoring module 36 need not be turned off when the patient begins eating and turned on again and reset when the patient has finished eating. It will be appreciated that the "disable" feature provided by the oximetry and capnography soft keys 140, 142 prevent nuisance alarms from occurring when one or more monitor modules 34, 36 are deliberately disconnected from the patient for a period of time. The "enable" feature, also provided by the soft keys 140, 142, allow the disabled monitor module to be rapidly and conveniently reinstated without having to power up the monitoring module and re-enter alarm limits.

In another feature in accordance with aspects of the invention, the rules for processing data in the controller may be dependent upon all physiological data concerning the patient that is provided. Should certain physiological data become unavailable or newly available during data processing, the rules of the PCA control Protocol may require that alarm and pause thresholds be recalculated for the data that continues to be received. For example, if the PCA Control Protocol sets respiration rate thresholds for alarming while information concerning the SpO2 of the patient is available but the SpO2 module becomes disabled later, the PCA Control Protocol may automatically alter the respiration rate threshold for alarm.

In the above embodiment, pausing of the PCA pump is not based on alarms provided by the physiological monitors 34 and 36. The sets of rules in the monitor modules 34 and 36 are allowed to proceed in their normal operation of the monitor modules and they may provide alarms based on their internal rule sets. Individual monitoring modules 34 and 36 (FIG. 2) could be disconnected from the program module 32 and therefore also from the PCA Control Protocol by shutting down and/or removing the module. However, this method would have the disadvantage of not allowing the flexibility of letting the monitoring units continue their normal operation, including alarming, outside the PCA Control Protocol while avoiding nuisance pauses of the PCA infusion. Further in another embodiment, the PCA Control Protocol 82 could alarm and pause PCA administration based on instantaneous values (non-filtered) from the patient monitoring modules 34 and 36 as a backup. This method has the drawback of being subject to transient, short term fluctuations in monitoring data causing the PCA Control Protocol to create nuisance alarms and pauses.

The present invention has the advantage over the prior art that transient fluctuations in monitoring data are more unlikely to cause an unwanted PCA pause event (shut off). The monitoring modules 34 and 36 are allowed to alarm independently of the PCA Pause Protocol, so the monitors' behavior will be as expected from prior experience. With the monitoring units alarming before the PCA Control Protocol, it is possible that the monitors' alarms will awaken the patient 44 and avoid a respiratory depression event. Further, the ability to enable/disable 140 and 142 control of the PCA Control Protocol from a patient monitoring module, such as SpO2 module 34 and/or EtCO2 module 36, allows the avoidance of events that will activate the PCA Pause Protocol when it is unwanted. Such as when removing the EtCO2 cannula if a patient is eating.

Although SpO2 has been used herein in referring to blood-oxygen saturation, this is used as an example or embodiment only. Other devices or methods for the measurement of blood-oxygen saturation may exist or may be developed that will function well. Likewise, EtCO2 has been used herein also to refer to the level of carbon dioxide. Other devices or techniques for the measurement of this patient physiological parameter may also exist or may be developed in the future. Additionally, other patient physiological parameters may be measured in addition or in place of those used in the foregoing embodiments.

A person skilled in the art will recognize that the disclosed methods and apparatus are readily adaptable for broader application, including but not limited to other patient care systems and drug infusion pump systems. Moreover, as will also be appreciated by persons of ordinary skill in the art, any of an EtCO2 monitored drug delivery system, SpO2 monitored drug delivery system, and other systems, according to the present invention, may also be provided as stand alone integral units.

Although the present invention has been described in terms of certain preferred embodiments, other embodiments that are apparent to those of ordinary skill in the art are also within the scope of the invention. Accordingly, the scope of the invention is intended to be defined only by reference to the appended claims. While variations have been described and shown, it is to be understood that these variations are merely exemplary of the present invention and are by no means meant to be limiting.

What is claimed is:

1. A system for optimizing control over a PCA device configured to deliver medication, comprising:
    a medication delivery request device with which a request signal for delivery of the medication is provided;
    a physiological device configured to provide a physiological signal representative of physiological data;
    a first controller that receives the physiological signal, processes the physiological signal and provides a first alarm signal according to a first rule;
    a first alarm device that communicates the first alarm signal; and
    a second controller, separate from the first controller, that receives the request signal, receives the physiological signal, processes the request signal and the physiological signal and controls the operation of the PCA device according to the processing to deliver medication in accordance with a second rule, wherein the second rule is different from the first rule;
    wherein the second rule comprises a first limit and a second limit greater than the first limit;
    wherein, if a value of the physiological signal falls below the second limit, then the second controller generates a second alarm signal;
    wherein, if the value of the physiological signal falls below the first limit, then the second controller controls the PCA device to a non-delivery mode in which the PCA device does not deliver medication;
    wherein the first rule is more sensitive to transient, short term physiological and electrical artifacts in the physiological signal than the second rule, thereby resulting in the second controller controlling the PCA device to the non-delivery mode less frequently than the first controller generating the first alarm signal according to the first rule.

2. The system for optimizing control of claim 1 further comprising a second alarm device that communicates a second alarm in response to the second alarm signal.

3. The system for optimizing control of claim 1 wherein the physiological data device comprises a physiological monitor that measures a physiological parameter and provides the physiological signal representative of the measured parameter.

4. The system for optimizing control of claim 3 wherein the second controller controls the PCA device according to the processing to a non-delivery mode in which the PCA device does not deliver medication.

5. The system for optimizing control of claim 4 wherein the second controller provides a second alarm signal according to the second rule, and a second alarm device that communicates the second alarm signal.

6. The system for optimizing control of claim 1 further comprising a physiological parameter data base of previously-determined patient-specific data related to a physiological parameters, wherein:
    the database provides a data signal representative of data related to a previously-determined patient-specific physiological parameter;
    the second controller receives the request signal, receives the physiological signal, receives the data signal, and processes the request signal, the physiological signal, and the data signal, and controls the operation of the PCA device in response to the processing to deliver medication in accordance with the second rule.

7. The system for optimizing control of claim 6 wherein: the physiological data device further comprises a physiological monitor that measures a physiological parameter and provides the physiological signal representative of the measured parameter.

8. The system for optimizing control of claim 1 further comprising an input device with which to modify the second rule.

9. The system for optimizing control of claim 1 further comprising a remote server connected with the second controller, wherein the second controller receives a modification to the second rule from the remote server and processes in accordance with the modified second rule.

10. The system for optimizing control of claim 9 wherein the second controller receives further patient-specific data from the remote server and processes the patient-specific data, the request signal, the physiological signal, and controls the operation of the PCA device in accordance with the processing to deliver medication in accordance with the modified second rule.

11. The system for optimizing control of claim 10 wherein the second controller controls the PCA device according to the processing to a non-delivery mode in which the PCA device does not deliver medication.

12. The system for optimizing control of claim 1 wherein the second controller filters the physiological signal according to one or more of an moving average filter, a rate of change filter and cumulative average, an impulse response filter, a statistical filter, an adaptive filter, and a pharmacokinetic model.

13. The system for optimizing control of claim 12 wherein a parameter of a filter is adapted in accordance with historical data related to a physiological parameter.

14. The system for optimizing control of claim 13 wherein a parameter of a filter is adapted in accordance with concomitant data related to medication infusion.

15. A method for optimizing control over a PCA device configured to deliver medication, comprising:
    receiving a medication request signal for delivery of the medication;
    receiving a physiological signal representative of physiological data;
    processing the physiological signal with a first controller and providing a first alarm signal according to a first rule;
    communicating the first alarm signal; and
    processing the request signal and the physiological signal with a second controller separately from the first controller and controlling the operation of the PCA device according to the processing to deliver medication in accordance with a second rule, wherein the second rule is different from the first rule; wherein the second rule comprises a first limit and a second limit greater than the first limit;
    generating at the second controller, if a value of the physiological signal falls below the second limit, a second alarm signal;
    controlling by the second controller, if the value of the physiological signal falls below the first limit, the PCA device to a non-delivery mode in which the PCA device does not deliver medication;
    wherein the first rule is more sensitive to transient, short term physiological and electrical artifacts in the physiological signal than the second rule, thereby resulting in the second controller controlling the PCA device to the non-delivery mode less frequently than the first controller generating the first alarm signal according to the first rule.

16. The method for optimizing control of claim 15 wherein the step of receiving a physiological signal representative of physiological data comprises measuring a physiological parameter and providing a physiological signal representative of the measured parameter.

17. The method for optimizing control of claim 15 wherein the step of controlling the operation of the PCA device comprises controlling the PCA device to a non-delivery mode in which the PCA device does not deliver medication.

18. The method for optimizing control of claim 15 further comprising providing a second alarm signal according to the second rule to a second alarm device that communicates the second alarm signal.

19. The method for optimizing control of claim 15 further comprising receiving a physiological data signal by the second controller representative of physiological data from a physiological parameter database of previously-determined patient-specific data related to a physiological parameter; and processing the data signal, the request signal, the physiological signal by the second controller, and controlling the operation of the PCA device in response to the processing in accordance with the second rule.

20. The method for optimizing control of claim 19 wherein the step of receiving a physiological signal representative of physiological data comprises measuring a physiological parameter and providing a physiological signal representative of the measured parameter.

21. The method for optimizing control of claim 15 further comprising modifying the second rule by use of an input device connected with the second controller.

22. The method for optimizing control of claim 21 wherein: the step of modifying the second rule comprises modifying the second rule by a remote server; and
    processing by the second controller comprises processing in accordance with the modified second rule.

23. The method for optimizing control of claim 22 further comprising receiving further patient-specific data from the second server and processing the patient-specific data, the request signal, the physiological signal by the second controller and controlling the operation of the PCA device in accordance with the processing to deliver medication in accordance with the modified second rule.

24. The method for optimizing control of claim 23 wherein the step of controlling the PCA device comprises controlling the PCA device according to the processing to a non-delivery mode in which the PCA device does not deliver medication.

* * * * *